United States Patent [19]
Hayashi et al.

[11] Patent Number: 5,929,258
[45] Date of Patent: Jul. 27, 1999

[54] METHOD OF MANUFACTURING EPOXIDE

[75] Inventors: Toshio Hayashi, Kobe; Masahiro Wada, Nishinomiya; Masatake Haruta, Ikeda, all of Japan

[73] Assignees: Agency of Industrial Science and Technology, Tokyo; Nippon Shokubai Co., Ltd., Osaka, both of Japan

[21] Appl. No.: 08/996,878

[22] Filed: Dec. 23, 1997

[30] Foreign Application Priority Data

Dec. 25, 1996 [JP] Japan .................................. 8-346076

[51] Int. Cl.$^6$ .................................................. C07D 301/03
[52] U.S. Cl. .............................................................. 549/523
[58] Field of Search ............................................. 549/523

[56] References Cited

U.S. PATENT DOCUMENTS

| | | | |
|---|---|---|---|
| 2,143,371 | 1/1939 | Francon .................................. | 549/523 |
| 4,609,502 | 9/1986 | Khoobiar et al. ....................... | 558/320 |
| 4,849,537 | 7/1989 | Ramachandran ........................ | 558/319 |
| 4,990,632 | 2/1991 | Ramachandran et al. .............. | 549/532 |
| 5,008,412 | 4/1991 | Ramachandran et al. .............. | 549/523 |
| 5,008,414 | 4/1991 | Ramachandran et al. .............. | 549/523 |
| 5,623,090 | 4/1997 | Haruta et al. ........................... | 568/360 |

FOREIGN PATENT DOCUMENTS

| | | |
|---|---|---|
| 0336592 A1 | 10/1989 | European Pat. Off. . |
| 0372972 A1 | 6/1990 | European Pat. Off. . |
| 0709360 A1 | 5/1996 | European Pat. Off. . |

*Primary Examiner*—Bernard Dentz
*Attorney, Agent, or Firm*—Nixon & Vanderhye P.C.

[57] ABSTRACT

The method of manufacturing an epoxide according to the present invention includes: a dehydrogenation step 1, in which a gas A containing an alkane is dehydrogenated, producing a gas B which contains an alkene and hydrogen; an epoxidation step 2, in which the gas B is epoxidized by use of a gas C containing oxygen in the presence of a catalyst containing gold, producing a gas D which contains an epoxide and unreacted hydrogen and oxygen; a separation step 3, in which the epoxide is separated from the gas D, leaving a gas E; and an oxygen elimination step 4, in which oxygen and hydrogen contained in the gas E are allowed to react, eliminating the oxygen and leaving a gas F. At least part of the gas F (gas $F_1$) is recycled by returning it to the dehydrogenation step 1. Hydrogen produced in the dehydrogenation step 1 is consumed in the epoxidation step 2 and the oxygen elimination step 4, and thus does not build up in the system of reaction. Accordingly, it is not necessary to separate or eliminate the hydrogen from the system of reaction. In other words, a method can be provided which is industrially advantageous for continuously producing an epoxide from an alkane.

17 Claims, 4 Drawing Sheets

F I G. 1
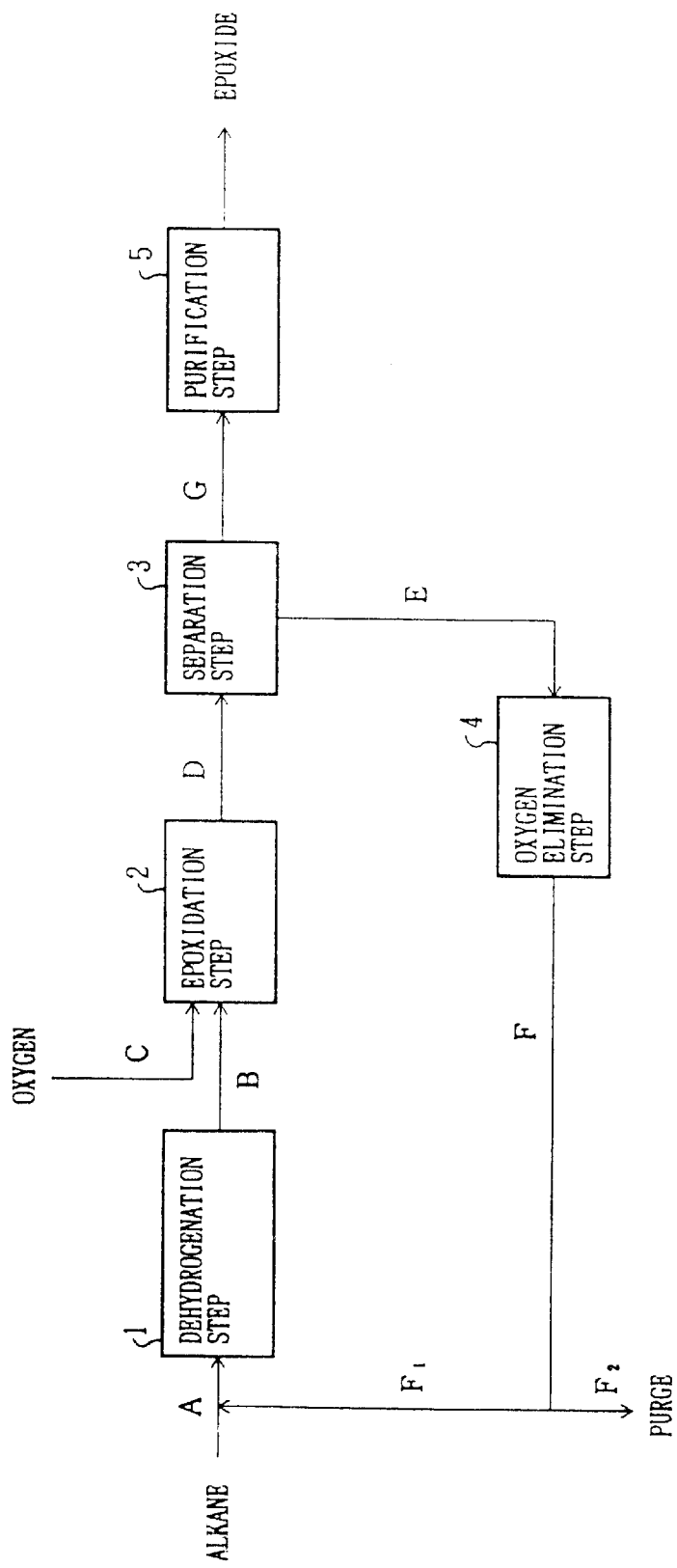

METHOD OF MANUFACTURING EPOXIDE

FIELD OF THE INVENTION

The present invention relates to a method of continuously manufacturing an epoxide (alkylene oxide), using an alkane as starting material, through an alkene, and relates to a catalyst for use in such a manufacturing method.

BACKGROUND OF THE INVENTION

As a method of industrial manufacture of propylene oxide (an epoxide), the chlorohydrine method or a direct oxidation method such as the halcon method or the peracetic acid method is used. However, the drawbacks of these methods are that they produce byproducts, and are two-stage manufacturing processes. As alternatives, various methods have been proposed of manufacturing propylene oxide by contact oxygen-oxidation (partial oxidation) of propylene (an alkene). However, these methods have performance problems, for example that the catalyst used has low selectivity for propylene oxide. Accordingly, these methods have not been implemented in industrial production.

Again, U.S. Pat. No. 5,623,090 (corresponding to Unexamined Japanese Patent Publication No. 8-127550/1996) discloses a method of using a vapor-phase oxidation reaction catalyst which contains gold and titanium oxide (titania) to oxygen-oxidize an alkene in the presence of hydrogen, thereby producing the corresponding epoxide. This method has high (about 90%) selectivity for the epoxide, but uses as starting material an alkene, which costs more than an alkane.

On the other hand, U.S. Pat. Nos. 4,990,632 and 5,008,412 disclose a continuous manufacturing method in which propane (an alkane) is dehydrogenated to produce propylene, and then the propylene is partially oxidized to produce propylene oxide. In this method, propane, which is cheaper than propylene, can be used as starting material. Further, this method recycles (reuses) unreacted propane and propylene. Again, U.S. Pat. No. 4,609,502 (corresponding to Unexamined Japanese Patent Publication No. 61-189256/1986) and U.S. Pat. No. 4,849,537 (corresponding to Unexamined Japanese Patent Publication No. 2-1449/1990), for example, disclose a method for producing an alkene by dehydrogenation of an alkane. In these methods, the alkene produced is then partially oxidized (ammoxidized) to produce a nitryl.

However, in the manufacturing methods disclosed in these two U.S. Patents, since the hydrogen which dehydrogenation produces along with the propylene is not consumed, recycling causes it to build up in the system of reaction. Accordingly, a feature of these methods is that they use a gas separation technique called PSA (pressure swing adsorption) to disperse or eliminate the hydrogen from the system of reaction. In other words, the complexity of the process of recycling unreacted hydrogen in these manufacturing methods makes it difficult to call them industrially advantageous.

For these reasons, a manufacturing method having high selectivity for an epoxide and a simplified process for recycling unreacted propane, etc., i.e., an industrially advantageous method for continuous production of an epoxide from an alkane, would be much welcomed.

SUMMARY OF THE INVENTION

The object of the present invention is to provide an industrially advantageous manufacturing method for continuous production of an epoxide from an alkane, and to provide a catalyst for use in such a manufacturing method.

The present inventor and others closely investigated an industrially advantageous manufacturing method for continuous production of an epoxide from an alkane. As a result, in a method for producing an epoxide from an alkane by (i) a dehydrogenation step, in which a gas A containing alkanes was dehydrogenated, thus producing a gas B containing alkenes, hydrogen, and unreacted alkanes, and (ii) an epoxidation step, in which oxygen and the gas B were allowed to react in the presence of a catalyst, thus producing a gas D containing epoxides, it was found that use of a catalyst containing gold in the epoxidation step enabled simple and efficient epoxidation of the alkenes, which improved the selectivity from the alkanes to the epoxides. The epoxides were then separated from the gas D produced in the epoxidation step, leaving a gas E. Oxygen was eliminated by allowing hydrogen and oxygen contained in the gas E to react, leaving a gas F containing unreacted alkanes. It was found that, by returning at least part of the gas F to the dehydrogenation step without removing the hydrogen contained therein, epoxides could be continuously produced from alkanes in an industrially advantageous manner, without separating or eliminating a large quantity of hydrogen from the system of reaction. In other words, it was found that since hydrogen produced in the dehydrogenation step was consumed in the epoxidation step, and remaining unreacted hydrogen was used to eliminate oxygen, there was no need for a step to separate or eliminate hydrogen from the system of reaction, thus simplifying the process for recycling the unreacted alkanes, etc., and making the method as a whole industrially advantageous. Thus the present invention was completed.

In other words, in order to attain the object mentioned above, the method of manufacturing an epoxide according to the present invention is one in which an epoxide is produced from an alkane by means of (i) a dehydrogenation step, in which a gas A containing an alkane is dehydrogenated, thus producing a gas B containing an alkene, hydrogen, and unreacted alkane, and (ii) an epoxidation step, in which the gas B is allowed to react with oxygen in the presence of a catalyst, thus producing a gas D containing an epoxide, and is characterized by the use of a catalyst containing gold in the epoxidation step.

Further, the method of manufacturing an epoxide according to the present invention is characterized by (iii) separation of the epoxide from the gas D produced in the epoxidation step, leaving a gas E, (iv) elimination of oxygen by allowing the hydrogen contained in the gas E to react with oxygen, leaving a gas F containing unreacted alkane, and (v) return of at least part of the gas F to the dehydrogenation step.

The method of manufacturing an epoxide according to the present invention is also characterized by performance of the dehydrogenation under the conditions of a temperature of 400° C. to 700° C. and a pressure of 0.1 bar. to 5 bar.

The method of manufacturing an epoxide according to the present invention is also characterized by performance of the epoxidation under the conditions of a hydrogen concentration of 2% to 40% by volume, an oxygen concentration of 2% to 40% by volume, an alkene concentration of 2% to 40% by volume, a temperature of 100° C. to 350° C., and a pressure of 0.1 bar. to 30 bar.

The epoxide manufacturing catalyst according to the present invention is the catalyst for manufacturing an epoxide used in the epoxidation step of the method of manufacturing an epoxide above, and is characterized in that it contains gold.

Since the catalyst used in the epoxidation step above (the epoxide manufacturing catalyst) contains gold, it has superior activity and selectivity in the epoxidation reaction in the presence of hydrogen. Accordingly, the alkene's selectivity for the epoxide can be improved. Further, since this catalyst consumes hydrogen during the epoxidation reaction, hydrogen produced in the dehydrogenation step can be used effectively. Hydrogen still remaining unreacted is then consumed in eliminating oxygen. In other words, hydrogen produced in the dehydrogenation step is consumed in the epoxidation step and the oxygen elimination step. Accordingly, even if at least part of the gas F is recycled by returning it to the dehydrogenation step without eliminating the hydrogen contained therein, hydrogen will not build up in the system of reaction. As a result, in the method above, a step for separating or eliminating a large quantity of hydrogen from the system of reaction is not needed, and the process for recycling unreacted alkane, etc. can be simplified, making the method as a whole more economical and industrially advantageous. This enables an epoxide to be continuously manufactured from an alkane, and at comparatively high yield.

Other objects, features, and strengths of the present invention will be made clear by the description below. In addition, the advantages of the present invention will be evident from the following explanations in reference to the attached drawings.

BRIEF DESCRIPTION OF THE DRAWINGS

FIG. 1 is a block diagram showing a schematic process of a method of manufacturing an epoxide according to one embodiment of the present invention.

DESCRIPTION OF THE EMBODIMENTS

Figure 2:
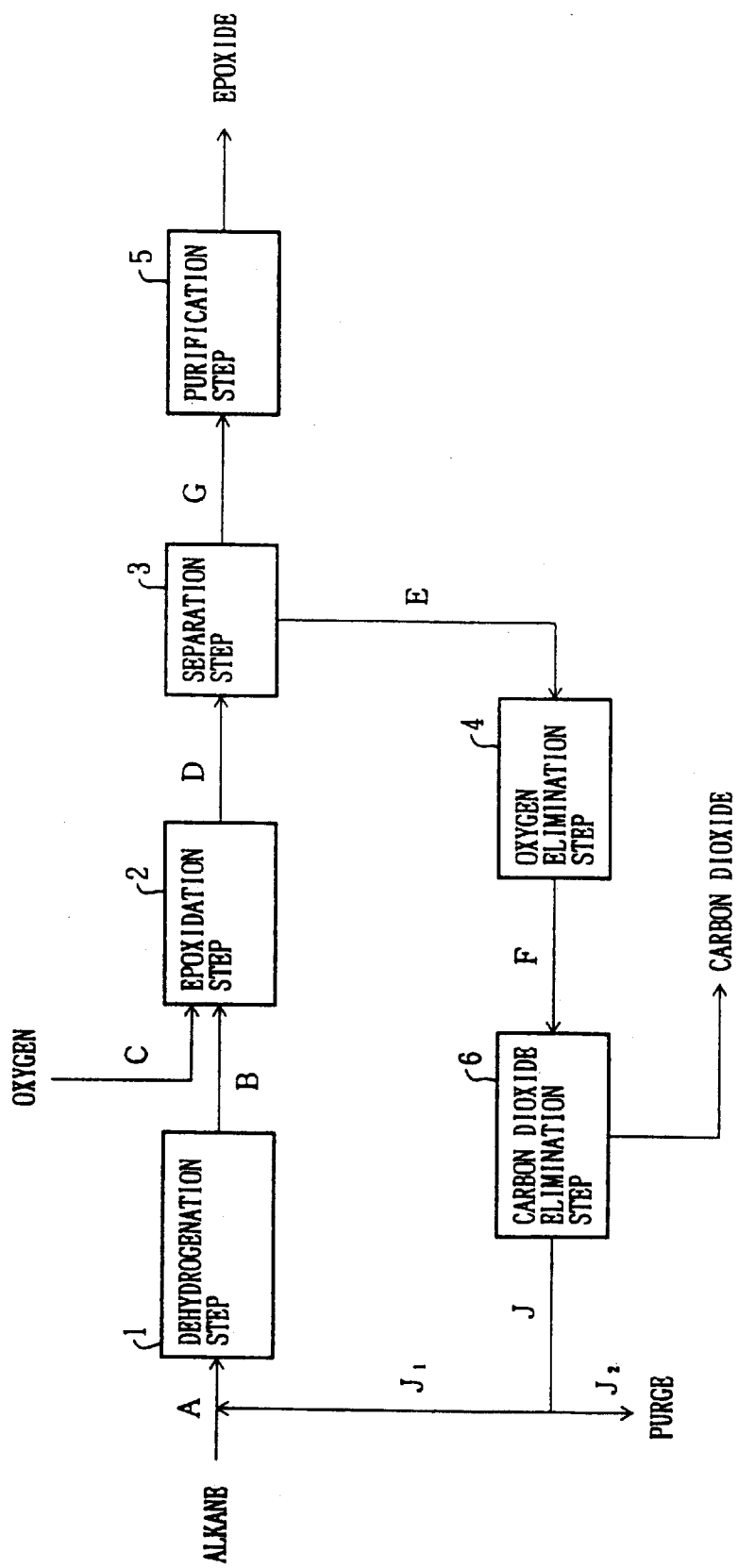
FIG. 2 is a block diagram showing a schematic process of a method of manufacturing an epoxide according to another embodiment of the present invention.

The method of manufacturing an epoxide according to the present invention is a method in which an epoxide is produced from an alkane by means of (i) a dehydrogenation step, in which a gas A containing an alkane is dehydrogenated, thus producing a gas B containing an alkene, hydrogen, and unreacted alkane, and (ii) an epoxidation step, in which the gas B is allowed to react with oxygen in the presence of a catalyst, wherein a catalyst containing gold is used in the epoxidation step. Further, it is a method in which (iii) the epoxide is separated from a gas D produced in the epoxidation step, thus leaving a gas E, (iv) oxygen is eliminated by allowing the hydrogen contained in the gas E to react with oxygen, thus leaving a gas F containing unreacted alkane, and (v) at least part of the gas F is returned to the dehydrogenation step.

The following will explain one embodiment of the present invention with reference to FIGS. 1 through 4.

As shown in FIG. 1, the method of manufacturing epoxide according to the present embodiment includes the steps of (i) a dehydrogenation step 1, in which a gas A containing an alkane is dehydrogenated, thus producing a gas B containing an alkene and hydrogen; (ii) an epoxidation step 2, in which the gas B is epoxidized by use of a gas C containing oxygen in the presence of a catalyst containing gold (catalyst for use in manufacturing epoxide), thus producing a gas D containing an epoxide and unreacted hydrogen and oxygen; (iii) a separation step 3, in which the epoxide is separated from the gas D; and (iv) an oxygen elimination step 4, in which oxygen is eliminated from a gas E produced in the separation step 3 by allowing the hydrogen and oxygen contained in the gas E to react; wherein at least part (shown by $F_1$ in FIG. 1) of a gas F produced in the oxygen elimination step 4 is recycled (reused) by returning it to the dehydrogenation step 1 without removing the hydrogen contained therein. In other words, the alkane is converted to the epoxide by reactions in two stages: dehydrogenation and epoxidation.

The alkane which is continuously supplied to the dehydrogenation step 1 as starting material is not limited to any particular alkane, but a compound with from 2 to 10 carbon atoms, inclusive, should preferably be used. In the present invention, "alkane" means a compound in which the chain portion is formed only of saturated bonds, and includes no unsaturated bonds. Accordingly, an alkane may have an aromatic ring as a substitution group. Thus, aromatic hydrocarbons having no unsaturated bonds except those forming the aromatic ring are considered alkanes in the present invention.

In concrete terms, the alkane used may be ethane, propane, n-butane, isobutane, n-hexane, n-octane, cyclohexane, ethyl benzene, isopropyl benzene, etc. By using the manufacturing method according to the present invention, the epoxides corresponding to the alkanes used can be obtained, yielding, for the examples above, ethylene oxide, propylene oxide, epoxy-butanes, 1,2-epoxy-2-methylpropane, epoxy-hexanes, epoxy-octanes, cyclohexene oxide, styrene oxide, and 1,2-epoxy-2-phenylpropane, respectively.

The gas A containing the alkane is not limited to a particular gas, but may be any mixture having an alkane concentration of from 10% to 100% by volume, preferably from 20% to 95% by volume. Gases other than alkane which may be contained in the gas A are not limited to any particular gases, but may include, for example, alkenes and hydrogen, or inert gases such as nitrogen, helium, argon, carbon dioxide, etc. Concrete examples of gases which may be used for gas A include distillates from petroleum reforming, waste gases produced by various reactions and operations, etc.

The catalyst used in the dehydrogenation step 1 to dehydrogenate the gas A containing the alkane (hereinafter referred to as the "dehydrogenation catalyst") should preferably be one in which a metal oxide made of an element such as chrome, iron, or molybdenum, or their mixtures, is supported by a carrier such as alumina, or in which a precious metal such as platinum is supported by a carrier such as alumina. However, the dehydrogenation catalyst is not limited to such a particular catalyst, and any catalyst typically used in dehydrogenation may be used. When the gas A is brought into contact with the dehydrogenation catalyst, a dehydrogenation reaction develops, and part of the alkanes contained in the gas A are converted into alkenes and hydrogen. Alkanes and alkenes with lower carbon numbers than the alkanes used as starting material (for example, methane, etc.) are also produced as byproducts. In other words, dehydrogenating the gas A produces the gas B, which contains alkenes, hydrogen, byproducts, and unreacted alkanes. The gas B is continuously supplied to the epoxidation step 2.

Dehydrogenation is an endothermic reaction. The reaction conditions of the dehydrogenation reaction may be set in accordance with the composition and quantity of the gas A supplied, the type and quantity of the dehydrogenation catalyst used, the combination of the gas A and the dehydrogenation catalyst, etc., and are not limited to any particular conditions, but it is preferable for the dehydrogenation reaction to have equilibrium, and for the reactive temperature to be within a range from 400° C. to 700° C. so as to easily control the dehydrogenation reaction, most preferably at around 600° C. Further, a reactive pressure within a range from 0.1 bar. to 5 bar. is preferable. The form of dehydrogenation may be any of fixed bed, fluidized bed, or moving bed.

The catalyst used in the epoxidation step 2 to epoxidize the gas B (hereinafter referred to as the "epoxidation catalyst") must contain gold, but is not otherwise limited to any particular catalyst. However, a catalyst which contains ultrafine gold particles 10 nm or less in average diameter and a metal oxide containing titanium (such as titania) is preferable. An epoxidation catalyst containing ultrafine gold particles and a metal oxide can be prepared, for example, by making the metal oxide carry the ultrafine gold particles. Such an epoxidation catalyst has especially good activity and selectivity. If the average diameter of the gold particles is more than 10 nm, the epoxidation catalyst is likely to have less activity than if their diameter is 10 nm or less. Further, there is no particular limitation on the diameter distribution of the gold particles, but a comparatively narrow distribution is preferable.

Since the epoxidation catalyst contains gold (preferably ultrafine gold particles and a metal oxide), it has superior activity and selectivity in the epoxidation reaction in the presence of hydrogen. In this epoxidation catalyst, because of the synergistic effect between the ultrafine particles of gold and the metal oxide, i.e., because these constituents exert their effects individually and synergistically, the alkene can be epoxidized simply and efficiently. Further, since the epoxidation catalyst has superior selectivity, the production of byproducts can be held to a lower level than in typical catalysts conventionally used in epoxidation. Accordingly, the epoxidation catalyst can improve the selectivity from the alkane to the epoxide.

The gas C which is continuously supplied to the epoxidation step 2 must contain oxygen, but is not otherwise limited to any particular gas. It is sufficient if the quantity of oxygen supplied is equal to or greater than the quantity required for epoxidation of the alkene in the gas B. Great oversupply of oxygen is not preferable, since it does not appreciably improve the activity and selectivity of the epoxidation catalyst, but makes operations in the oxygen elimination step 4 troublesome.

The gas C may, as necessary, contain gases inert to epoxidation and the other reactions of the present invention, such as nitrogen, helium, argon, carbon dioxide. In other words, the oxygen may, as necessary, be diluted by inert gases. Further, air may be used as the gas C.

By bringing the gas B into contact with the epoxidation catalyst in the presence of the gas C, i.e., by bringing a mixture of the gases B and C into contact with the epoxidation catalyst, an epoxidation reaction develops, and part of the alkenes contained in the gas B is converted into epoxides. Since hydrogen produced in the dehydrogenation step 1 is consumed by the epoxidation catalyst in the epoxidation reaction, the hydrogen can be used effectively. Byproducts produced are aldehyde and ketone, or water (water vapor), carbon dioxide, etc. In other words, epoxidizing the gas B produces a gas D which contains epoxides, byproducts, unreacted alkanes and alkenes, hydrogen, and oxygen. The gas D is continuously supplied to the separation step 3. Incidentally, most of the hydrogen and oxygen are consumed in the epoxidation reaction using the epoxidation catalyst, but some hydrogen and oxygen remain as unreacted substances in the gas D. Further, in cases where the gas C contains inert gases, the gas D also contains these inert gases.

The reaction conditions of the epoxidation reaction may be set in accordance with the composition and quantity of the gases B and C supplied, the type and quantity of the epoxidation catalyst used, the combination of the gases B and C and the epoxidation catalyst, etc., and are not limited to any particular conditions, but, in order for at least the alkanes, alkenes, and epoxides to remain in a gaseous state, the reactive temperature should preferably be within a range from 100° C. to 350° C., more preferably between 120° C. and 280° C. Further, the reactive pressure should preferably be within a range from 0.1 bar. to 30 bar. In the mixture of gases B and C, a hydrogen concentration of 2% to 40% by volume, an oxygen concentration of 2% to 40% by volume, and an alkene concentration of 2% to 40% by volume are preferable. Incidentally, the sum of these hydrogen, oxygen, and alkene concentrations will not exceed 100% by volume. The form of epoxidation may be any of fixed bed, fluidized bed, or moving bed.

The method of separating the epoxides from the gas D in the separation step 3 is not limited to any particular method, but a suitable method is one in which, for example, an organic solvent, water, etc. and the gas D are brought into efficient gas-liquid contact by a mixing operation such as counterflow, thereby causing the epoxides to be dissolved (absorbed) into the organic solvent, water, etc. The organic solvent used is not limited to any particular organic solvent, but may be any compound able to dissolve the epoxides, but having low activity with respect to the epoxides and low dissolution with respect to the unreacted alkanes, alkenes, etc. Further, the water may be a water solution in which alkylene diol, etc. is dissolved. The operating conditions at the time of the epoxide separation may be set in accordance with the composition and quantity of the gas D supplied, the type and quantity of the organic solvent, water, etc. (hereinafter referred to simply as "solvent") used, the combination of the gas D and the solvent, etc., and are not limited to any particular conditions, but conditions allowing at least the alkanes and alkenes to remain in a gaseous state are preferable. In the separation step 3, byproducts such as aldehyde and ketone and part of the water are also separated from the system of reaction.

The solvent G containing the epoxide is supplied to the purification step 5. In the purification step 5, the epoxide contained in the solvent G is separated and recovered by, for example, an operation such as distillation. Then, as necessary, the epoxide recovered is purified by means of an operation such as distillation (rectification). In this way, an epoxide of high purity can be obtained. The method of distillation is not limited to any particular method, and may be continuous or repetitive. Further, the solvent from which the epoxide has been separated may be recycled by returning it to the separation step 3.

The gas E from which the epoxide has been separated in the separation step 3 is continuously supplied to the oxygen elimination step 4. In other words, in the oxygen elimination step 4, oxygen (i.e., oxygen gas) is eliminated from the gas E containing byproducts, unreacted alkanes and alkenes, hydrogen, and oxygen. If oxygen is present in the dehydrogenation step 1, the efficiency of dehydrogenation of the gas A is markedly reduced. Accordingly, in the oxygen elimination step 4, oxygen is eliminated by allowing oxygen and hydrogen contained in the gas E to react with one another. If necessary, a quantity of hydrogen necessary to eliminate the oxygen in the oxygen elimination step 4 may be added to the gas C and/or the gas B. When the gas E does not contain enough hydrogen to eliminate all of the oxygen, the remaining oxygen can be eliminated by allowing it to react with byproducts such as methane, or with alkene. Again, when the gas D contains inert gases, the gas E also contains these inert gases.

The catalyst used in the oxygen elimination reaction to eliminate the oxygen (hereinafter referred to as the "oxidation catalyst") is not limited to any particular catalyst, but a suitable catalyst is, for example, one containing a Group VIII precious metal such as platinum or palladium, or one containing ultrafine gold particles 10 nm or less in diameter. By bringing the gas E into contact with the oxidation catalyst, an oxidation reaction, i.e., a reaction between hydrogen and oxygen, develops, producing water (water vapor). Alternatively, a reaction (complete oxidation reaction) between oxygen and byproducts (such as methane) or alkenes develops, producing water (water vapor) and carbon dioxide. In other words, oxygen is eliminated from the gas E.

It is best if the unreacted hydrogen in the gas E is entirely consumed in the oxygen elimination reaction. However, in order to entirely consume the oxygen, it is usually more advantageous from an operations standpoint to use a quantity of hydrogen exceeding the quantity theoretically required. Accordingly, in actual practice, a small amount of hydrogen may remain in the gas F. In this case, since part or most of the gas F is recycled by returning it to the dehydrogenation step 1, the hydrogen remaining in the gas F is supplied to the dehydrogenation step 1. However, since the dehydrogenation reaction has equilibrium, a small amount of hydrogen remaining in the gas F will not cause any insurmountable problem in the dehydrogenation step 1.

The reaction conditions of the oxygen elimination reaction may be set in accordance with the composition and quantity of the gas E supplied, the type and quantity of the oxidation catalyst used, the combination of the gas E and the oxidation catalyst, etc., and are not limited to any particular conditions, but conditions allowing at least the alkanes and alkenes to remain in a gaseous state are preferable. The form of the oxygen elimination reaction may be any of fixed bed, fluidized bed, or moving bed. By means of the oxygen elimination reaction, the gas F is produced, which contains unreacted alkanes and alkenes, and byproducts such as carbon dioxide and water. When the gas E contains inert gases, the gas F also contains these inert gases.

The gas F is continuously returned to the dehydrogenation step 1 along with new alkanes. In other words, by continuously returning the gas F to the dehydrogenation step 1, the unreacted alkanes and alkenes contained in the gas F can be recycled. Accordingly, the gas A is a mixture of alkanes and at least part of the gas F.

The entirety of the gas F may be returned to the dehydrogenation step 1, but, in order to prevent buildup of byproducts and inert gases in the system of reaction, it is preferable to release from the system of reaction, i.e., to purge, part (shown by $F_2$ in FIG. 1) of the gas F. Purge of the gas $F_2$ may be carried out continuously or intermittently.

The quantity of the gas F purged from the system of reaction, i.e., the quantity of the gas $F_2$, (hereinafter the "purged quantity") may be set according to the composition of the gas F, etc., and is not limited to any specific quantity, but it is preferable to set the purged quantity to a level such that byproducts and inert gases will not build up in the system of reaction, and such that the quantity of alkanes and alkenes purged along with the byproducts and inert gases is as small as possible. The purged quantity should preferably be within a range from 0.1% to 10% by volume of the total quantity, more preferably within a range from 1% to 5% by volume of the total quantity. In other words, of the gas F, 90% to 99.9% by volume, more preferably 95% to 99% by volume, should be returned to the dehydrogenation step 1. If the purged quantity is less than 0.1% by volume, byproducts, inert gases, etc. are likely to build up in the system of reaction. Again, if the purged quantity is more than 10% by volume, the quantity of alkanes and alkenes purged along with the byproducts, inert gases, etc. is increased, which is economically disadvantageous.

If byproducts (such as methane) or alkenes are used to eliminate oxygen in the oxygen elimination step 4, the gas F will contain more carbon dioxide than if hydrogen alone is used to eliminate oxygen. In this case, it is preferable to eliminate carbon dioxide from the gas F.

In other words, when the gas F has a comparatively high carbon dioxide content, it is preferable to eliminate the carbon dioxide by performing a carbon dioxide elimination step 6 during the period between the oxygen elimination step 4 and the dehydrogenation step 1, as shown in FIG. 2. In this case, the gas F is continuously supplied to the carbon dioxide elimination step 6. The method of eliminating carbon dioxide in the carbon dioxide elimination step 6 is not limited to any particular method, but a suitable method is one in which, for example, a water solution of an alkaline metal hydroxide such as potassium hydroxide and the gas F are brought into efficient gas-liquid contact by a mixing operation such as counterflow, thereby causing the alkaline metal hydroxide and the carbon dioxide to react, producing an alkaline metal carbonate.

The operating conditions at the time of the oxygen elimination may be set in accordance with the composition and quantity of the gas F supplied, the type of the alkaline metal hydroxide, the concentration and quantity of the water solution used, the combination of the gas F and the alkaline metal hydroxide, etc., and are not limited to any particular conditions, but conditions allowing at least the alkanes and alkenes to remain in a gaseous state are preferable. In the carbon dioxide elimination step 6, the carbon dioxide in the gas F may be completely eliminated, or enough may be eliminated to bring the carbon dioxide concentration of the gas F down to a predetermined level. Incidentally, in the carbon dioxide elimination step 6, part of the water, which is a byproduct, is eliminated from the system of reaction.

The gas J, from which the carbon dioxide has been eliminated in the carbon dioxide elimination step 6, is continuously returned to the dehydrogenation step 1 along with new alkanes. In other words, by continuously returning the gas J to the dehydrogenation step 1, the unreacted alkanes and alkenes contained in the gas J can be recycled. Accordingly, when the carbon dioxide elimination step 6 is performed, the gas A is a mixture of alkanes and at least part of the gas J.

The entirety of the gas J may be returned to the dehydrogenation step 1, but, in order to prevent buildup of byproducts and inert gases in the system of reaction, it is preferable to purge from the system of reaction part (shown by $J_2$ in FIG. 2) of the gas J, and return the remainder (shown by $J_1$ in FIG. 2) to the dehydrogenation step 1. Purge of the gas $J_2$ may be carried out continuously or intermittently.

The purged quantity of the gas J may be set according to the composition of the gas J, etc., and is not limited to any specific quantity, but it is preferable to set the purged quantity to a level such that byproducts and inert gases will not build up in the system of reaction, and such that the quantity of alkanes and alkenes purged along with the byproducts and inert gases is as small as possible. The purged quantity should be within a range from 0.1% to 10% by volume of the total quantity, more preferably within a range from 1% to 5% by volume of the total quantity. In other words, of the gas J, 90% to 99.9% by volume, more preferably 95% to 99% by volume, should be returned to the dehydrogenation step 1. If the purged quantity is less than 0.1% by volume, byproducts, inert gases, etc. are likely to build up in the system of reaction. Again, if the purged quantity is more than 10% by volume, the quantity of alkanes and alkenes purged along with the byproducts, inert gases, etc. is increased, which is economically disadvantageous.

After separation from the gas J, the water solution containing (dissolving) the alkaline metal carbonate is, for example, heated. By this means, the alkaline metal carbonate is decomposed into an alkaline metal hydroxide and carbon dioxide. In other words, the carbon dioxide is separated and recovered by heating the water solution containing the alkaline metal carbonate. The method of separating and recovering the carbon dioxide is not limited to any specific method, and may be continuous or intermittent. The water solution from which the carbon dioxide has been separated may be recycled by returning it to the carbon dioxide elimination step 6.

As discussed above, the method of manufacturing an epoxide according to one embodiment of the present invention is a method including: a dehydrogenation step 1, in which a gas A containing an alkane is dehydrogenated, thus producing a gas B containing an alkene and hydrogen; an epoxidation step 2, in which the gas B is epoxidized by use of a gas C containing oxygen in the presence of an epoxidation catalyst, thus producing a gas D containing an epoxide and unreacted hydrogen and oxygen; a separation step 3, in which the epoxide is separated from the gas D, thus leaving a gas E; and an oxygen elimination step 4, in which oxygen is eliminated by allowing the hydrogen and oxygen contained in the gas E to react with one another; wherein at least part of a gas F from which the oxygen has been eliminated is returned to the dehydrogenation step 1.

Since the epoxidation catalyst contains gold, it has superior activity and selectivity. Accordingly, the alkene's selectivity for the epoxide can be improved. Further, since the epoxidation catalyst consumes hydrogen during the epoxidation reaction, hydrogen produced in the dehydrogenation step 1 can be used effectively. Hydrogen still remaining unreacted is consumed in the elimination of oxygen in the oxygen elimination step 4. In other words, hydrogen produced in the dehydrogenation step 1 is consumed in the epoxidation step 2 and the oxygen elimination step 4. Accordingly, even if at least part of the gas F (gas $F_1$) is recycled by continuously returning it to the dehydrogenation step 1, hydrogen will not build up in the system of reaction. As a result, in this method, a step for separating or eliminating hydrogen from the system of reaction is not needed, thus simplifying the process for recycling unreacted alkane, etc., which makes the method as a whole more economical and industrially advantageous. Thus an epoxide can be continuously manufactured from an alkane, and at comparatively high yield.

Next, an example of a manufacturing device suited to implementation of one embodiment of the manufacturing method according to the present invention will be explained with reference to FIG. 3. The following explanation will discuss an example in which the alkane is propane, i.e., in which propane is used as starting material for continuous manufacturing of propylene oxide as the epoxide.

Figure 3:
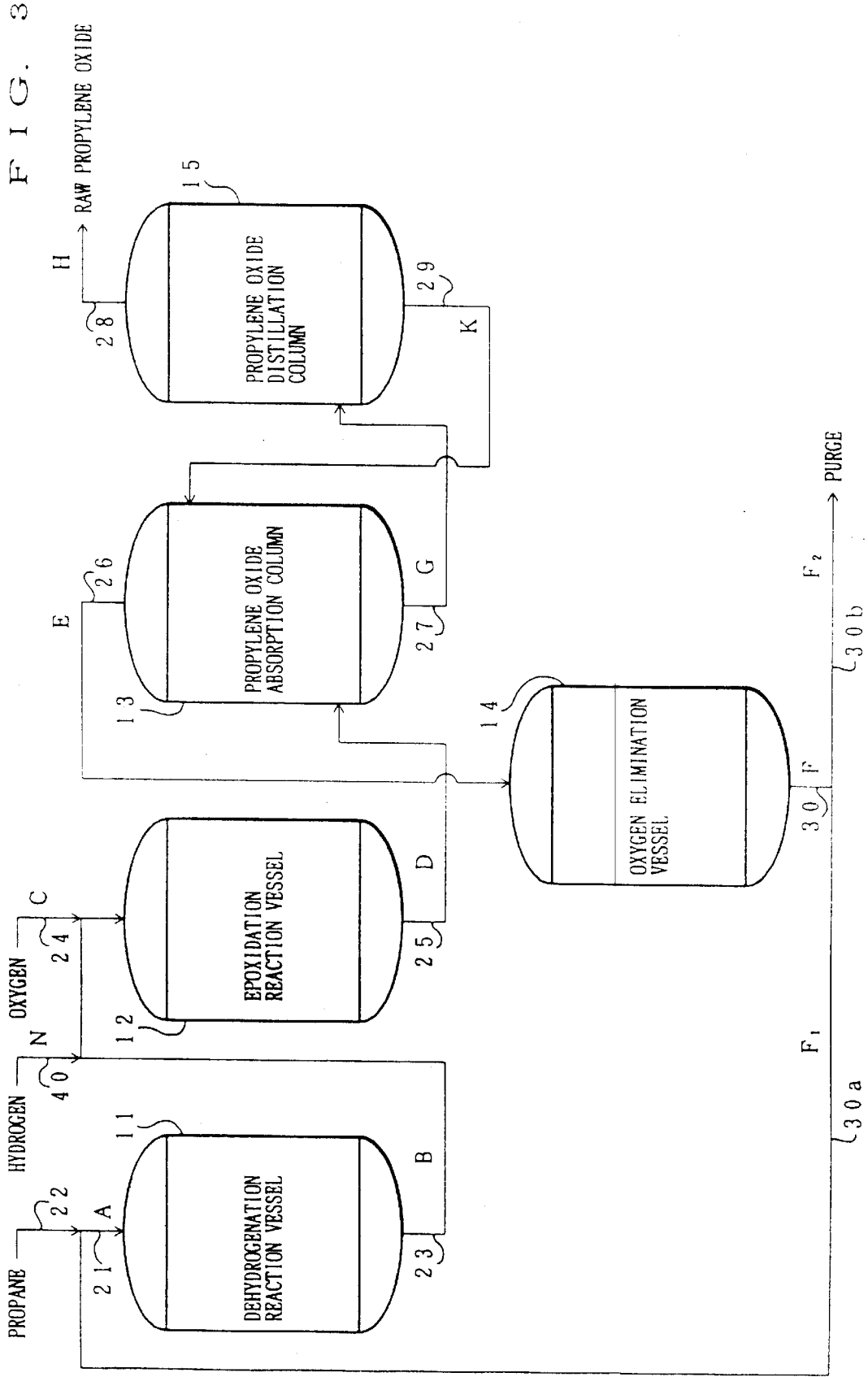
FIG. 3 is a block diagram showing an example of a manufacturing device suited to implementation of the process shown in FIG. 1.

As shown in FIG. 3, this manufacturing device is provided with a dehydrogenation reaction vessel 11 where the dehydrogenation step 1 is performed, an epoxidation reaction vessel 12 where the epoxidation step 2 is performed, a propylene oxide absorption column 13 where the separation step 3 is performed, an oxygen elimination vessel 14 where the oxygen elimination step 4 is performed, and a propylene oxide distillation column 15 where the purification step 5 is performed.

The dehydrogenation reaction vessel 11 is, for example, a fixed-bed reaction vessel, and brings the gas A into contact with the dehydrogenation catalyst. The interior of the dehydrogenation reaction vessel 11 is supplied with the dehydrogenation catalyst. A gas A supply pipe 21 is connected to the upper part of the dehydrogenation reaction vessel 11. The gas A supply pipe 21 is connected to a propane supply pipe 22, which continuously supplies new propane to the dehydrogenation reaction vessel 11, and to a recycling pipe 30a, which continuously returns the gas $F_1$ to the dehydrogenation reaction vessel 11. In the gas A supply pipe 21 near the dehydrogenation reaction vessel 11 is provided a thermal exchanger (not shown), which heats the gas A. To the lower part of the dehydrogenation reaction vessel 11 is connected a gas B supply pipe 23, which continuously supplies the gas B to the epoxidation reaction vessel 12. At a predetermined location in the gas B supply pipe 23 is provided a thermal exchanger (not shown), which cools the gas B. Accordingly, in the dehydrogenation reaction vessel 11, the gas A is sent through a down-flow.

In the dehydrogenation reaction vessel 11, from around 10% to 60% by mole (depending on the dehydrogenation reaction conditions) of the propane in the gas A is dehydrogenated, converting it to propylene and hydrogen, and producing as byproducts methane, ethane, ethylene, etc. (hereinafter referred to as "light boiling point components"). The conversion of the propane in the dehydrogenation reaction vessel 11 is from around 10% to 60% by mole, and the selectivity to propylene is from 92% to 98% by mole. Accordingly, from 40% to 90% by mole of the propane in the gas A is contained in the gas B as unreacted propane.

The epoxidation reaction vessel 12 is, for example, a fixed-bed reaction vessel, and brings the mixture of the gas B and the gas C into contact with the epoxidation catalyst. The interior of the epoxidation reaction vessel 12 is supplied with the epoxidation catalyst. The gas B supply pipe 23 is connected to the upper part of the epoxidation reaction vessel 12. The gas B supply pipe 23 is also connected to a gas C supply pipe 24, which continuously supplies the gas C to the epoxidation reaction vessel 12, and to a gas N supply pipe 40, which supplies, as necessary, a gas N containing hydrogen to the epoxidation reaction vessel 12. To the lower part of the epoxidation reaction vessel 12 is connected a gas D supply pipe 25, which continuously supplies the gas D to the propylene oxide absorption column 13. Accordingly, in the epoxidation reaction vessel 12, the gas B is sent through a down-flow. The flows of the gases B, C, and, as necessary, N are regulated so that the epoxidation reaction vessel 12 contains, for every mole of propylene, from 0.2 mol to 20 mol of hydrogen and from 0.2 mol to 20 mol of oxygen.

In the epoxidation reaction vessel 12, from around 2% to 50% by mole (depending on the epoxidation reaction conditions) of the propylene in the gas B is epoxidized, converting it to propylene oxide, and producing as byproducts carbon dioxide, water, etc. The conversion of the propylene in the epoxidation reaction vessel 12 is from around 2% to 50% by mole, and the selectivity to propylene oxide is 80% by mole or better. Accordingly, from 50% to 98% by mole of the propylene in the gas B is contained in the gas D as unreacted propylene.

The propylene oxide absorption column 13 is an absorption column of the gas-liquid contact type, and brings the gas D into gas-liquid contact with a solvent. The gas D supply pipe 25 is connected to the propylene oxide absorption column 13 near the column's bottom. To the lower part of the propylene oxide absorption column 13 is connected a solvent G supply pipe 27, which continuously supplies a solvent G containing the propylene oxide to the propylene oxide distillation column 15. Further, to the upper part of the propylene oxide absorption column 13 is connected a gas E supply pipe 26, which continuously supplies the gas E to the oxygen elimination vessel 14. Near the top of the propylene oxide absorption column 13 is connected a solvent K supply pipe 29, which continuously supplies to the propylene oxide absorption column a solvent K, from which raw propylene oxide has been separated in the propylene oxide distillation column 15. Accordingly, in the propylene oxide absorption column 13, the gas D and the solvent are sent through a counterflow.

The oxygen elimination vessel 14 is, for example, a fixed-bed reaction vessel, and brings the gas E into contact with the oxidation catalyst. The interior of the oxygen elimination vessel 14 is supplied with the oxidation catalyst. To the upper part of the oxygen elimination vessel 14 is connected the gas E supply pipe 26. To the lower part of the oxygen elimination vessel 14 is connected a gas F emptying pipe 30, which empties the gas F from the oxygen elimination vessel 14. The gas F emptying pipe 30 branches into the recycling pipe 30a and a purge pipe 30b, which purges the gas $F_2$. Accordingly, in the oxygen elimination vessel 14, the gas E is sent through a down-flow.

The propylene oxide distillation column 15 is, for example, a continuous multi-stage distillation column, and continuously separates and recovers the propylene oxide from the solvent G. The solvent G supply pipe 27 is connected to the propylene oxide distillation column 15 at substantially the center stage of the column. To the upper part of the propylene oxide distillation column 15 is connected an extraction pipe 28, which continuously extracts from the propylene oxide distillation column 15 raw propylene oxide in a gaseous state. To the lower part of the propylene oxide column 15 is connected the solvent K supply pipe 29. At a predetermined location in the extraction pipe 28 is provided a condenser (not shown), which condenses the raw propylene oxide. Further, the extraction pipe 28 is connected to a purification column (not shown). In the purification column, propylene oxide and compounds having boiling points close to propylene oxide, such as propion aldehyde and acetone, are continuously separated from the gas H.

Figure 4:
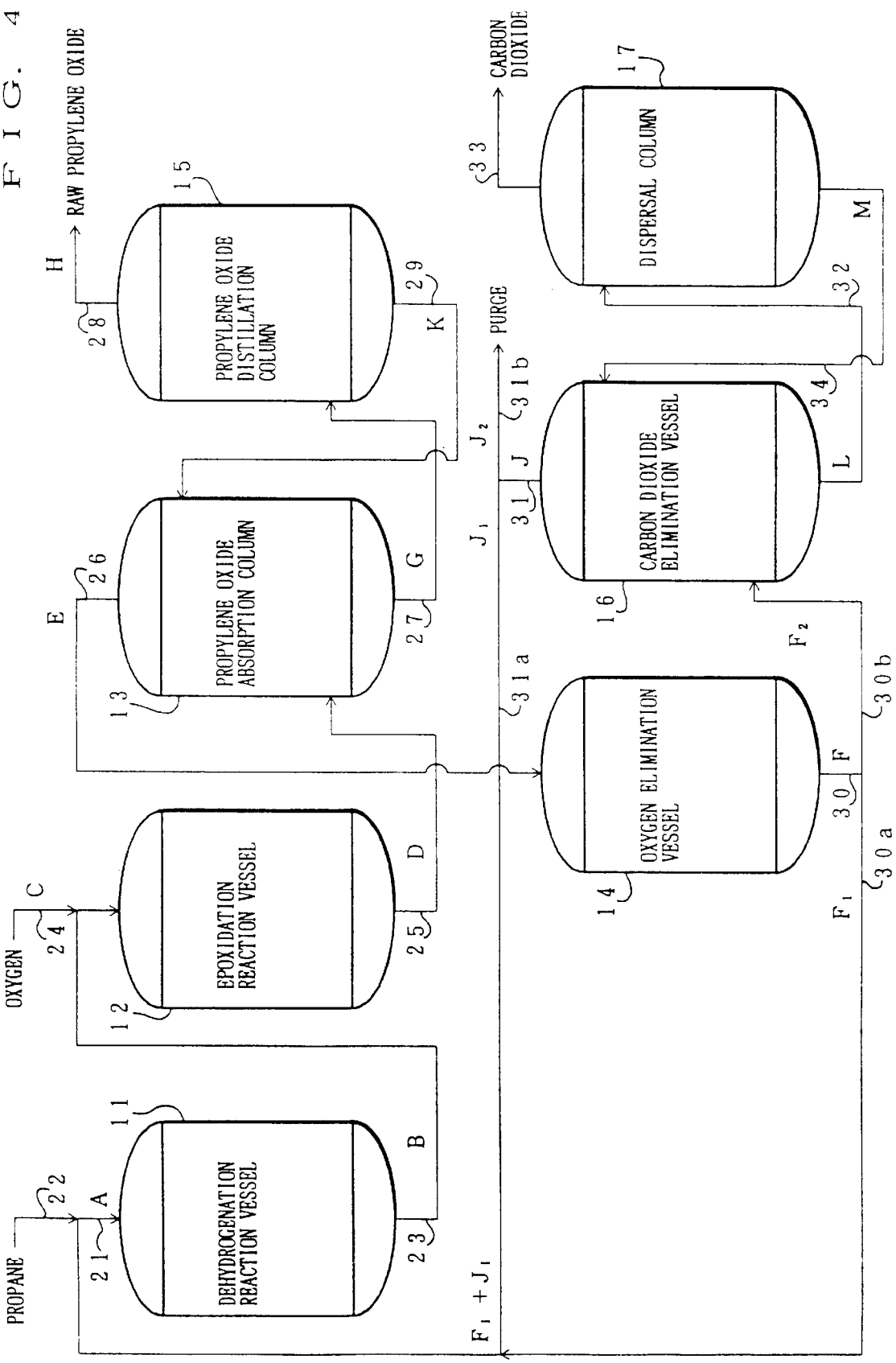
FIG. 4 is a block diagram showing an example of a manufacturing device suited to implementation of the process shown in FIG. 2.

In cases where the gas F has a comparatively high carbon dioxide content, it is preferable if the manufacturing device explained above is further provided with a carbon dioxide absorption column 16 and a dispersal column 17, which perform the carbon dioxide elimination step 6, as shown in FIG. 4.

The carbon dioxide absorption column 16 is an absorption column of the gas-liquid contact type, and brings the gas $F_2$ into gas-liquid contact with a water solution containing an alkaline metal hydroxide. Near the bottom of the carbon dioxide absorption column 16 is connected the purge pipe 30b, from which the gas $F_2$ is continuously supplied. To the lower part of the carbon dioxide absorption column 16 is connected a water solution L supply pipe 32, which continuously supplies to the dispersal column 17 a water solution L containing an alkaline metal carbonate. Further, to the upper part of the carbon dioxide absorption column 16 is connected a gas J emptying pipe 31, which empties the gas J from the carbon dioxide absorption column 16. The gas J emptying pipe 31 branches into a recycling pipe 31a, which continuously returns the gas $J_1$ to the dehydrogenation reaction vessel 11, and a purge pipe 31b, which purges the gas $J_2$. The recycling pipe 31a is connected to the recycling pipe 30a, and accordingly a mixture of gases $F_1$ and $J_1$ is continuously returned to the dehydrogenation reaction vessel 11. Near the top of the carbon dioxide absorption column 16 is connected a water solution M supply pipe 34, which continuously supplies the water solution M. Accordingly, in the carbon dioxide absorption column 16, the gas $F_2$ and the water solution are sent through a counterflow.

By heating the water solution L, the dispersal column 17 continuously decomposes the alkaline metal carbonate into an alkaline metal hydroxide and carbon dioxide. Near the top of the dispersal column 17 is connected the water solution L supply pipe 32. To the upper part of the dispersal column 17 is connected an extraction pipe 33, which continuously extracts the carbon dioxide. To the lower part of the dispersal column 17 is connected the water solution M supply pipe 34.

By using a manufacturing device with the foregoing structure, propylene oxide can be produced from propane continuously and at comparatively high yield. Incidentally, the manufacturing device may have a plurality of dehydrogenation reaction vessels 11. In this case, the dehydrogenation reaction vessels 11 are connected in parallel. The manufacturing device may also have a plurality of epoxidation reaction vessels 12. In this case, the epoxidation reaction vessels 12 are connected in parallel.

Next, the specific embodiments of the present invention will be explained in more detail, but these embodiments are not to limit the present invention in any way.

FIRST EMBODIMENT

In this embodiment, the elimination of oxygen in the oxygen elimination step was actually performed by means of a reaction between hydrogen and oxygen alone, and, in order to prevent buildup of byproducts, etc. such as carbon dioxide, part of the recycle gas was purged. In other words, propylene oxide was produced continuously from propane using the manufacturing device shown in FIG. 3.

The flow of propane supplied to the dehydrogenation reaction vessel 11 through the propane supply pipe 22 was set at 52.8 mol/hr. After heating the gas A (a mixture of the propane and the gas $F_1$) by means of a thermal exchanger, it was continuously supplied to the dehydrogenation reaction vessel 11. The flow of the gas A was 1,292 mol/hr, and its composition by volume was: 18.6% propane, 16.9% propylene, 6.6% carbon dioxide, 2.2% light boiling point components, 2.0% water, 0.4% hydrogen, and 53.4% nitrogen (inert gas).

A chromia-alumina catalyst was used for the dehydrogenation catalyst. The dehydrogenation reaction vessel 11 supplied with this catalyst was operated at a reaction temperature of 600° C. and a reaction pressure of 1.0 bar.

Analysis of the gas B found that the conversion of the propane was 17%, and that the selectivity to propylene was 97%.

After cooling the gas B with a thermal exchanger, hydrogen, oxygen, and nitrogen were mixed with the gas B, and this mixture was continuously supplied to the epoxidation reaction vessel 12. Specifically, the epoxidation reaction vessel 12 was supplied with hydrogen through the gas N supply pipe 40, etc. at a flow of 29.3 mol/hr, and with oxygen and nitrogen through the gas C supply pipe 24, etc. at flows of 55 mol/hr and 44 mol/hr, respectively.

A catalyst of ultrafine gold particles supported by titania-silica was used for the epoxidation catalyst. The epoxidation reaction vessel 12 supplied with this catalyst was operated at a reaction temperature of 200° C. and a reaction pressure of 5 bar. The flow of the gas D was 1,430 mol/hr, and its composition by volume was: 13.9% propane, 16.2% propylene, 1.7% propylene oxide, 6.3% carbon dioxide, 2.1% light boiling point components, 5.2% water, 2.2% hydrogen, 0.9% oxygen, and 51.3% nitrogen. Accordingly, the conversion of the propylene was 10%, and the selectivity to propylene oxide was 93%.

The gas D was supplied continuously to the propylene oxide absorption column 13 with no reduction in pressure. Then, the propylene oxide absorption column 13 was operated at a temperature of 40° C., a pressure of 5 bar., and with a water (solvent K) flow of approximately 800 mol/hr. The water solution (solvent G), continuously supplied to the propylene oxide distillation column 15 through the solvent G supply pipe 27, contained 24.2 mol/hr of propylene oxide. This propylene oxide was able to be continuously separated in the propylene oxide distillation column 15.

The flow of the gas E was 1,332 mol/hr, and its composition by volume was: 15.0% propane, 17.4% propylene, 0.0% propylene oxide, 6.8% carbon dioxide, 2.2% light boiling point components, 2.4% hydrogen, 1.0% oxygen, and 55.1% nitrogen. The gas E was continuously supplied to the oxygen elimination vessel 14.

A catalyst of platinum supported by alumina was used for the oxidation catalyst. The oxygen elimination vessel 14 supplied with this catalyst was operated at a reaction temperature of 180° C. Analysis of the gas F found that it contained no oxygen, but contained carbon dioxide (6.9% by volume) and light boiling point components (2.3% by volume), and hydrogen (0.4% by volume), etc. The gas F was divided into $F_1$ and $F_2$, so that the ratio between their volumes (gas $F_1$:gas $F_2$) was 94:6, and the gas $F_1$ was continuously supplied to the dehydrogenation reaction vessel 11, while the gas $F_2$ was purged.

By performing the above operations, unreacted propane and propylene were able to be recycled without buildup of byproducts, etc., such as carbon dioxide and light boiling point components, in the system of reaction. As a result, propylene oxide was able to be produced continuously from propane.

SECOND EMBODIMENT

In this embodiment, the elimination of oxygen in the oxygen elimination step was performed by means of a reaction between hydrogen and oxygen and a reaction between light boiling point components and oxygen, and, in order to prevent buildup of byproducts, etc. such as carbon dioxide, a carbon dioxide elimination step and a purge were performed. In other words, propylene oxide was produced continuously from propane using the manufacturing device shown in FIG. 4.

The flow of propane supplied to the dehydrogenation reaction vessel 11 was set at 36.8 mol/hr. After heating the gas A (a mixture of the propane and the gases $F_1$ and $J_1$) by means of a thermal exchanger, it was continuously supplied to the dehydrogenation reaction vessel 11. The flow of the gas A was 981 mol/hr, and its composition by volume was: 18.3% propane, 25.2% propylene, 4.2% carbon dioxide, 5.1% light boiling point components, 1.3% water, 0.0% hydrogen, and 45.9% nitrogen.

A catalyst of platinum and tin supported by alumina was used for the dehydrogenation catalyst. The dehydrogenation reaction vessel 11 supplied with this catalyst was operated at a reaction temperature of 600° C. and a reaction pressure of 0.8 bar. Analysis of the gas B found that the conversion of the propane was 18%, and that the selectivity to propylene was 96%.

After cooling the gas B with a thermal exchanger, oxygen and nitrogen were mixed with the gas B, and this mixture was continuously supplied to the epoxidation reaction vessel 12. Specifically, the epoxidation reaction vessel 12 was supplied with oxygen and nitrogen through the gas C supply pipe 24, etc. at flows of 50 mol/hr and 14 mol/hr, respectively.

A catalyst of ultrafine gold particles supported by titania-silica was used for the epoxidation catalyst. The epoxidation reaction vessel 12 supplied with this catalyst was operated at a reaction temperature of 200° C. and a reaction pressure of 5 bar. The flow of the gas D was 1,057 mol/hr, and its composition by volume was: 14.0% propane, 24.5% propylene, 1.7% propylene oxide, 4.3% carbon dioxide, 4.9% light boiling point components, 4.2% water, 0.5% hydrogen, 2.0% oxygen, and 43.9% nitrogen. Accordingly, the conversion of the propylene was 7%, and the selectivity to propylene oxide was 92%.

The gas D was supplied continuously to the propylene oxide absorption column 13 with no reduction in pressure. Then, the propylene oxide absorption column 13 was operated at a temperature of 40° C., a pressure of 5 bar., and with a water flow of approximately 800 mol/hr. The water solution, continuously supplied to the propylene oxide distillation column 15 through the solvent G supply pipe 27, contained 18.1 mol/hr of propylene oxide. This propylene oxide was able to be continuously separated in the propylene oxide distillation column 15.

The flow of the gas E was 995 mol/hr, and its composition by volume was: 14.8% propane, 26.0% propylene, 0.0% propylene oxide, 4.6% carbon dioxide, 5.2% light boiling point components, 0.6% hydrogen, 2.1% oxygen, and 46.6% nitrogen. The gas E was continuously supplied to the oxygen elimination vessel 14.

A catalyst of platinum supported by alumina was used for the oxidation catalyst. The oxygen elimination vessel 14 supplied with this catalyst was operated at a reaction temperature of 220° C. Analysis of the gas F found that it contained neither oxygen nor hydrogen, but contained carbon dioxide (5.8% by volume) light boiling point components (5.2% by volume), etc. Further, it was found that hydrogen, propylene, and light boiling point components such as ethyl were consumed in the elimination of oxygen. The gas F was divided into $F_1$ and $F_2$, so that the ratio between their volumes (gas $F_1$:gas $F_2$) was 70:30, and the gas $F_1$ was continuously supplied to the dehydrogenation reaction vessel 11, while the gas $F_2$ was continuously supplied to the carbon dioxide absorption column 16.

The gas J, from which carbon dioxide was eliminated in the carbon dioxide absorption column 16, was then divided into $J_1$ and $J_2$, so that the ratio between their volumes (gas $J_1$:gas $J_2$) was 90:10, and the gas $J_1$ was continuously supplied to the dehydrogenation reaction vessel 11, while the gas $J_2$ was purged. Accordingly, 3% by volume of the components (excluding carbon dioxide) of the gas F were purged as the gas $J_2$. In other words, 97% by volume of the components of the gas F (excluding carbon dioxide) were recycled as the gases $F_1$ and $J_1$.

By performing the above operations, unreacted propane and propylene were able to be recycled without buildup of byproducts, etc., such as hydrogen, carbon dioxide and light boiling point components, in the system of reaction. As a result, propylene oxide was able to be produced continuously from propane.

The concrete examples of implementation and the embodiments discussed in the foregoing detailed explanations of the present invention serve solely to illustrate the technical details of the present invention, which should not be narrowly interpreted within the limits of such concrete examples, but rather may be applied in many variations without departing from the spirit of the present invention and the scope of the patent claims set forth below.

What is claimed is:

1. A method of manufacturing an epoxide from an alkane comprising the steps of:

(i) dehydrogenating a gas A containing the alkane so as to produce a gas B containing alkene, hydrogen, and unreacted alkane; and (ii) causing oxygen and the gas B, including the hydrogen produced in step (i), to react in the presence of a catalyst, so as to produce the epoxide;

wherein the catalyst used in step (ii) contains gold.

2. The method of manufacturing an epoxide set forth in claim 1, wherein:

the catalyst used in said step (ii) contains ultrafine gold particles and a metallic oxide containing titanium.

3. The method of manufacturing an epoxide set forth in claim 1, wherein:

the gas A contains a concentration of the alkane which is within a range from 10% to 100% by volume.

4. The method of manufacturing an epoxide set forth in claim 1, wherein:

the alkane has from 2 to 10 carbon atoms, inclusive.

5. The method of manufacturing an epoxide set forth in claim 1, wherein:

the alkane is propane.

6. The method of manufacturing an epoxide set forth in claim 1, wherein:

said step (ii) is performed under the conditions of a hydrogen concentration of 2% to 40% by volume, an oxygen concentration of 2% to 40% by volume, an alkene concentration of 2% to 40% by volume, a temperature of 100° C. to 350° C., and a pressure of 0.1 bar. to 30 bar.

7. The method of manufacturing an epoxide set forth in claim 1, wherein:

the epoxide is separated from a gas D produced in said step (ii) so as to leave a gas E;

oxygen and hydrogen contained in the gas E are allowed to react so as to eliminate the oxygen and produce a gas F containing unreacted alkanes; and at least part of the gas F is returned to said step (i).

8. The method of manufacturing an epoxide set forth in claim 7, wherein:

90% to 99.9% by volume of the gas F is returned to said step (i).

9. The method of manufacturing an epoxide set forth in claim 7, wherein:

part of the gas F is purged.

10. The method of manufacturing an epoxide set forth in claim 7, wherein:

carbon dioxide is eliminated from the gas F.

11. The method of manufacturing an epoxide set forth in claim 7, wherein:

carbon dioxide is eliminated from the gas F so as to leave a gas J, at least part of which is returned to said step (i).

12. The method of manufacturing an epoxide set forth in claim 11, wherein:

90% to 99.9% by volume of the gas J is returned to said step (i).

13. The method of manufacturing an epoxide set forth in claim 11, wherein:

part of the gas J is purged.

14. The method of manufacturing an epoxide set forth in claim 1, wherein:

said step (i) is performed under the conditions of a temperature of 400° C. to 700° C. and a pressure of 0.1 bar. to 5 bar.

15. The method of manufacturing an epoxide set forth in claim 1, wherein:

said catalyst is titania-silica carrying ultrafine gold particles.

16. A method of manufacturing an epoxide as in claim 1 wherein in step (ii) hydrogen is also added to the gas B.

17. A method to form an epoxide from an unreacted alkane comprising the steps of:

(i) dehydrogenating a gas A containing the unreacted alkane to produce a gas B containing an alkene, hydrogen, and unreacted alkane;

(ii) reacting oxygen with the gas B to in the presence of a catalyst containing gold to produce a gas C containing the epoxide, hydrogen and oxygen;

(iii) consuming at least a portion of the hydrogen in gas B during the reaction of step (ii);

(iv) separating the expoxide from the gas C to form a gas D containing oxygen, hydrogen and unreacted alkane;

(v) reacting the oxygen in gas D with the hydrogen from gas D to form a gas E including unreacted alkane; and (v) adding at least a portion of gas E to gas A prior to the dehydrogenation step (i).

* * * * *